(12) United States Patent  (10) Patent No.: US 7,878,990 B2
Al-Obaidi et al.  (45) Date of Patent: Feb. 1, 2011

(54) GAIT TRAINING DEVICE AND METHOD

(76) Inventors: Saud M. Al-Obaidi, Faculty of Allied Health Sciences, Departement of Physical Therapy, Kuwait University, P.O. Box 31470, Sulibikhate 90805 (KW); Fawzi Behbehani, PO Box 2943, Safat (KW) 13030

( * ) Notice: Subject to any disclaimer, the term of this patent is extended or adjusted under 35 U.S.C. 154(b) by 171 days.

(21) Appl. No.: 11/360,591

(22) Filed: Feb. 24, 2006

(65) Prior Publication Data

US 2007/0202478 A1  Aug. 30, 2007

(51) Int. Cl.
*A61B 5/103* (2006.01)
(52) U.S. Cl. ...................................... 600/592
(58) Field of Classification Search ................. 600/595, 600/592
See application file for complete search history.

(56) References Cited

U.S. PATENT DOCUMENTS

| | | | |
|---|---|---|---|
| 4,647,918 A * | 3/1987 | Goforth | 340/573.1 |
| 5,042,504 A * | 8/1991 | Huberti | 600/592 |
| 5,337,757 A * | 8/1994 | Jain et al. | 600/592 |
| 6,039,658 A * | 3/2000 | Cecchin | 473/269 |
| 6,836,744 B1 * | 12/2004 | Asphahani et al. | 702/141 |
| 7,191,644 B2 * | 3/2007 | Haselhurst et al. | 73/172 |
| 2003/0216621 A1 * | 11/2003 | Alpert et al. | 600/300 |
| 2004/0173220 A1 * | 9/2004 | Harry et al. | 128/892 |
| 2007/0021689 A1 * | 1/2007 | Stergiou et al. | 600/595 |

OTHER PUBLICATIONS

"A piezoresistive GaAs pressure sensor with GaAs/AlGaAs membrane technology," J. Micromech. Mircoeng, 5 (1995) 139-142.*

* cited by examiner

*Primary Examiner*—Max Hindenburg
*Assistant Examiner*—Michael C Stout
(74) *Attorney, Agent, or Firm*—Lowe Hauptman Ham & Berner, LLP

(57) ABSTRACT

A gait training device includes a pair of weight sensors with one of the sensors placed under each foot of an individual. The device also includes a microcomputer and a pair of electrical cables connecting each of the weight sensors to the microcomputer. A control panel/display is connected to the microcomputer and includes a pair of monitors for displaying target loads and/or actual loads averaged over a number of gait cycles for each foot. An audio alarm is also provided and sounds each time that a target load is exceeded. Methods for analyzing and correcting excess forces on an injured limb are also disclosed.

1 Claim, 3 Drawing Sheets

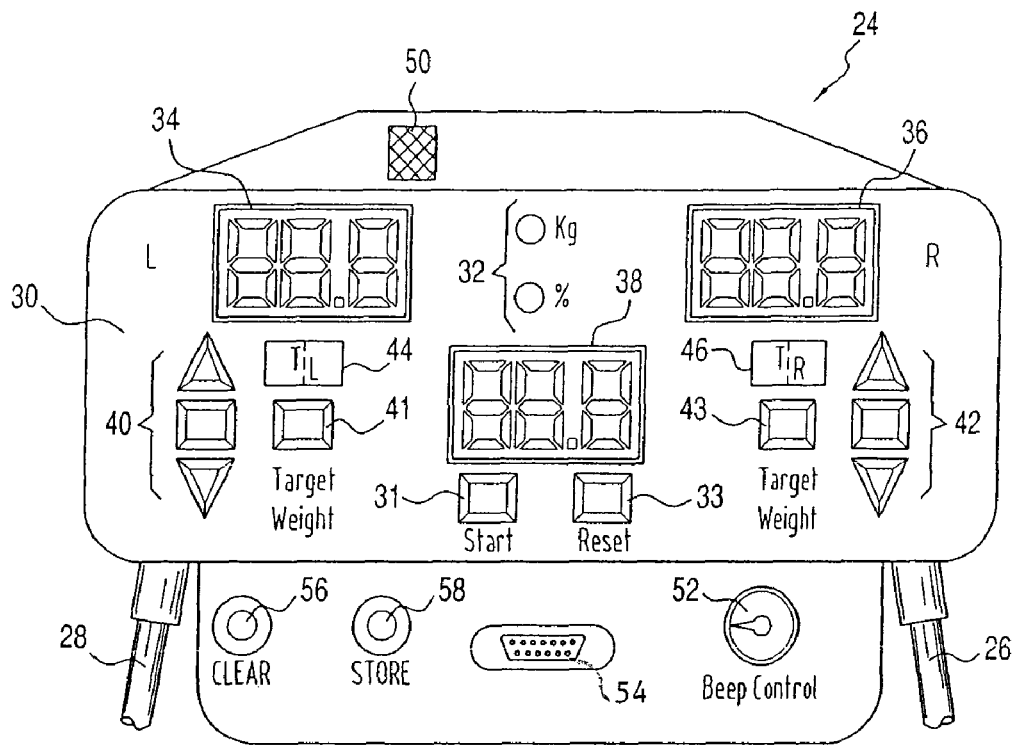
FIG. 2
FIG. 3
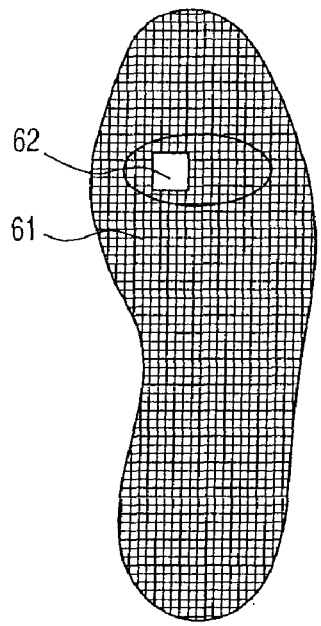
FIG. 4
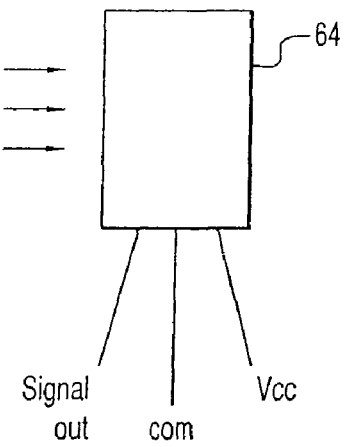

GAIT TRAINING DEVICE AND METHOD

FIELD OF THE INVENTION

This invention relates to a gait training device and method and more particularly to a gait training device and method for detecting and correcting improper weight distribution during movement of an individual's body as for example during walking.

BACKGROUND FOR THE INVENTION

Hip replacement surgery was first performed in 1960 and is considered to be one of the most important surgical advances of the century. Since then improvements in joint replacement, surgical techniques and technology have increased the effectiveness of this surgery. Today, more than 172,221 total hip replacements are performed each year in the United States according to the American Academy of Orthopedic Surgeons. It has also been reported that over 250,000 Americans undergo knee replacement surgeries each year. This surgical procedure was first performed in 1968 and typically relieves knee pain and restores joint function.

Today orthopedists and researchers recognize that placing some force on healing bones of the lower extremity following surgery, fracture or replacement stimulates bone healing. However, excessive force may result in the delayed healing or malunion of the bone. Therefore, for each fracture and location of fracture an optimal and measurable range of force should be placed across the fracture to maximize bone healing. Further, the peak force should be monitored in each gait cycle to be certain that it does not exceed a maximum limit prescribed by a physician. When physicians provide written orders to physical therapists regarding ambulatory training, they may prescribe "partial weight bearing status". Such instructions are vague and may result in too much or too little force being applied to the affected limb. This may result in damage to the limb or less than optimal healing. Accordingly, there is a need for monitoring weight bearing on a limb during movement of the body.

An orthopedic weight monitor for detecting weight bearing forces on a lower extremity for orthopedic purposes is disclosed in a U.S. Pat. No. 5,253,654 of Thomas et al. As described therein a flexible pad is shaped to conform to the bottom of a foot for placement inside of a shoe or cast. The pad has a heel portion for placement beneath the heel of a user, a sensor is incased within the heel portion of a pad to be located beneath the heel of the user. An electronic module is remotely positioned from the sensor to receive signals from the sensor.

A more recent development is shown in a U.S. Patent of Wanderman et al., U.S. Pat. No. 5,511,561 that discloses a gait cycle force monitor to detect the amount of force translated through a patient's heel in each gait cycle. The foot-pad has a tactile force sensor, means to translate a force applied to the sensor, a comparator and an annunciater. The comparator which can be analog or microprocessor controlled has a set point and an amplifier that is activated when the voltage from the sensor exceeds the set point. The piezo-electric annunciater is driven by the amplifier to warn the patient that excessive force is being translated through the heel.

Notwithstanding the above it is presently believed that there is a need and a potential commercial market for an improved gait training device and method in accordance with the present invention. There should be a need and commercial market for such devices that provide dynamic measure and weight distribution between the patient's lower extremities.

The devices in accordance with the present invention also measure the weight under each heel in each gait, and may provide a more natural gait during testing. Further, it is presently believed that such devices may be particularly applicable for testing and treating disorders and or injuries to the lower spine.

In addition to the above, the devices and methods in accordance with the present invention can be manufactured and sold at a competitive price, are durable and easily used by physical therapists.

BRIEF SUMMARY OF THE INVENTION

In essence the present invention contemplates a gait training device for detecting and correcting improper weight distribution during movement of an individual's body as for example in walking. The device includes two weight sensors one of which is attached to the underside of each foot for producing an output signal indicative of the amount of weight placed on the foot during walking. The device also includes a microcomputer and means for inputting pre-selected weights into the computer's memory. A pair of cables connects the weight sensors to the microcomputer and means including the microcomputer compare the pre-selected weights and the sensed weights. Means for indicating differences between the pre-selected weight and the sensed weights are also provided. In addition, in a preferred embodiment of the invention, the microcomputer and software include means for averaging the sensed weights and for storing the results in the computer memory for retrieval by a clinician.

The invention also contemplates a method for a physical therapists to objectively identify the percentage of a target weight for each limb and to train a patient to work within the percentages of the target weights and to safely monitor and control the load that can and should be tolerated on each foot. The method in accordance with the present invention contemplates a dynamic gait training method for detecting and correcting improper weight distribution during walking and includes the steps of providing two weight sensors and attaching one weight sensor under each foot of a individual being tested or treated. The method also includes the steps of providing a microcomputer and two cables for connecting the weight sensors to the microcomputer. Target weights for each foot are inputted into the microcomputer.

In the preferred embodiment of the invention, the weight percentages under each foot are compared with inputted weight percentages during multiple cycles. The results are then stored in memory for subsequent analysis by a clinician and review with the individual or patient for corrective action.

DESCRIPTION OF THE DRAWINGS

FIG. 2 is a front elevational view of a control panel as used in a preferred embodiment of the invention;

FIG. 3 is a top or plan view illustrating sensitive electronic load sensors made up of multiple arrays of displacement transistors as disposed in one embodiment of the invention;

FIG. 4 is a schematic illustration of a displacement transistor as used in the present invention.

DESCRIPTION OF THE PREFERRED EMBODIMENTS OF THE INVENTION

Figure 1:
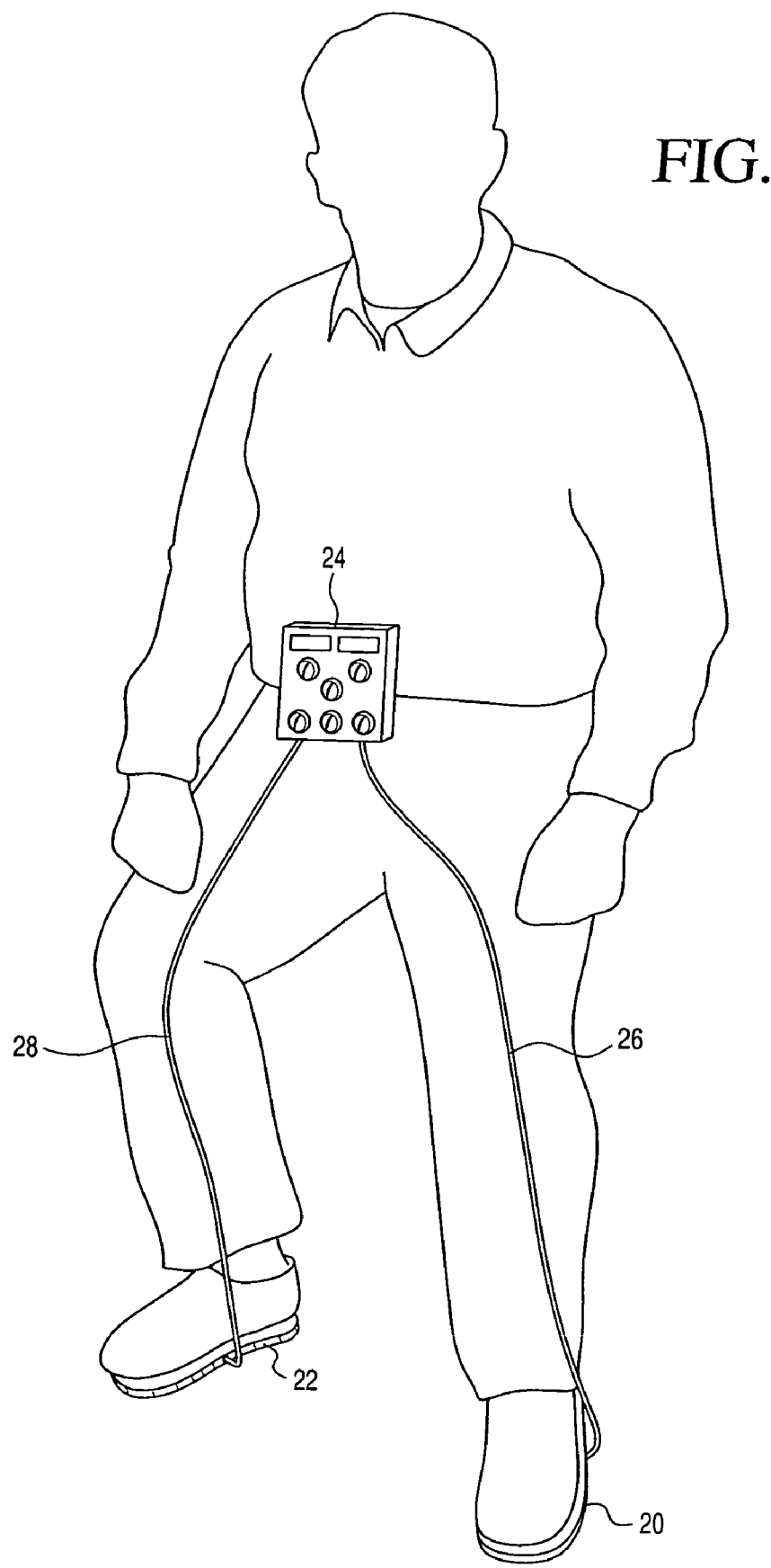
FIG. 1 is a schematic illustration of a gait training device for detection and/or correcting improper weight distribution during a walking exercise in accordance with a first embodiment of the invention.

A gait training device in accordance with the present invention is essentially a pressure sensor device that senses the pressure under each foot of an individual during a walking exercise. The device converts a mechanical signal from the actual body weight force on each foot to an electrical signal that is displayed on two monitors, one for each foot that reports the actual body weight under each foot during the exercise.

Theoretically, in healthy individuals with no musculoskeletal injuries involving the lower back or the lower extremities, the body weight is equally distributed through the spine to both hips and knees to the ankles and feet. At the level of the foot, the body weight is spread between the rear foot and the front foot. In reality if two identical and well calibrated bathroom scales were to be placed under the feet of a healthy individual in relaxed erect standing posture each scale would read 50% of the total body weight.

However, as an individuals lean to support their body weight on one limb, the bathroom scale reading under the supporting limb will increase due to the shifting of the body weight towards that side which will increase the total percentage of the body weight supported by that side. Walking is a cyclical event and single limb support is subconsciously taking place twice in every successful heal to heal event or a single stride. In addition, walking is a highly automated movement and involves interaction between central and peripheral nervous systems.

From a clinical perspective, the fear of pain and re-injury of the lower extremities usually disturb the symmetrical and coordination of the weight bearing mechanism on the feet during standing or walking. This forces the body to compensate by exaggerating the joint excursion and the time and distant perimeters of the walking cycle of the other lower extremity joints or excessively loading the joints of the feet which ultimately predispose for further maladattive behavior. If not treated, this will result in a walking deficit and mechanical impairment involving the lower extremities. Re-training a patient to bear symmetrical weight on both feet during walking is a challenging clinical experience specifically after severe fracture injuries or painful trauma involving the lower extremities or the spine.

In clinical management of orthopedic conditions in which patients are not allowed to bear full weight bearing on the foot, the clinician has to depend on the patient's abilities and compliance to train themselves on the target or acceptable weight bearing load. In clinical practice, non-weight bearing means that the patient is not allowed to place his effective foot on the floor, but in partial weight bearing with only part of the effected foot or partial weight is permitted to touch the floor has not been defined or calibrated into objective scores. The gait training device in accordance with the present invention is an ideal monitoring and re-training device that is designed to help a clinician to identify objectively the percentage of the target weight for each limb and train the patient to work within the percentage of that target weight and to safely monitor and control the load that can be tolerated by each foot.

A therapist needs to identify the percentage of the target load to train the patient with and to increase the percentage of the target weight in time as the patient builds up some weight bearing tolerance. The gait training device disclosed herein helps the clinician to be reliable in their load bearing training prescription in exercises specifically and works particularly well with fractures of lower extremities that require partial weight bearing. All that the therapist has to do is to decide on the appropriate percentage of target weight for training. The target weight is derived from the measured or estimated body weight of the patient and dividing the number equally between the two lower extremities. The target weight is a hypothetically percentage of load bearing that has to be decided by the therapist on a scale of load percentage ranging between two percent to 100% of the optimal body weight of a given limb with an increment of two kg. The optimal body weight on each limb is theoretically half the estimated or measured body weight.

The gait training device disclosed herein is useful for a wide range of clinical applications specifically for patients with joint disease, fractures, total replacement, or other conditions that require limitation of weight bearing. It is specifically useful for patients whose cognitive status prevents self monitoring. The device can be set and programmed on a specific target load bearing percentage and maintained on that percentage by monitoring or during a clinical setting for weight bearing re-training exercises. The device has another feature built in which allows clinicians to monitor a complete weight bearing data per time frame. This means that each time the patients load the effective feet, the device will store the unsuccessful weight attempt on the right or left limb during a given time frame. This will allow clinicians and patients to review and correct the load bearing ability during walking with the ability to transfer the data from the gait-training device to a personal computer. Further the device as disclosed herein is lightweight and may include insoles for different sizes and comes with its cable connections, sole sensors, batteries and instruction manuals. Table one is an example of rating available from a device in accordance with the present invention.

TABLE 1 explanation of a print of data istory downloaded from GTD to computer

| Step Time | | Right Foot 100% Target Load | Left Foot 20% Target | Buzzer | Loads registered |
|---|---|---|---|---|---|
| R | L | 100 | 0 | off | |
| | .20 ms | 82 | 19 | on | |
| .20 ms | | 100 | 0 | off | |
| | | 80 | 20 | | |
| | | 100 | 0 | on | |
| | | 79 | 25 | on | Left Exceed by 5 kg |

As illustrated in FIG. 1, a gait training device in accordance with the first embodiment of the invention includes a pair of weight sensors 20 and 22 with one of the sensors placed under each foot of an individual or patient. In practice, the weight sensors 20 and 22 may be placed in an insole which is placed in the patient's shoe. Each weight sensor 20 and 22 may also be a single sensor placed under the heel or an of array of displacement transistors as shown in FIG. 3. In the latter case, each transistor converts mechanical pressure into an electrical signal. The electrical signals are then sent to the microcomputer 24 by means of a pair of electrical cables 26 and 28 which connects the sensors 20 and 22 to the microcomputer 24. The microcomputer 24 sums the electrical signals from each of the sensors 20 and 22, calculates and indicates the force applied by each foot during one or more gait cycles. Such calculations and indications are performed by straightforward software that is well within the ability of a person of ordinary skill in the art. Further, in the case of a single or several sensors under the heel of each foot, a simple circuit may be used in place of the microcomputer.

The microcomputer 24 also includes or is connected to a control panel 30. The control panel 30 shown in FIG. 2 includes displayed selected means 32 for selecting and indication and actual weight or in percentages of total body weight when measuring the forces applied during each gait cycle. The control panel 30 also includes a left monitor or display 34 and a right monitor or display 36 for displaying the forces being applied by each foot of the patient. Such forces may be displayed in absolute weights or percentage of optimal load. The display may also display average forces applied during multiple gait cycles.

A timer 38 includes an indicator, a start button 31 and a reset button 33 which is used to measure the time of a session including multiple gait cycles. The control panel also includes a pair of target rate selectors 40 and 42 for selecting target weights for each foot. Each of the selectors include an up and down arrow for increasing or decreasing a target weight.

The target weight for the left foot is displayed in a window 41 while the target rate for the right foot is displayed in a window 43. In a preferred embodiment of the invention, the control panel 30 also includes a pair of window displays 44 and 46 for displaying the time for the gait cycle for each leg. The windows 44 and 46 may be divided into two areas for displaying the time that each leg spends in a stance phase and a swing phase averaged over a number of gait cycles. The stance phase is a period of time during which a foot is in contact with the ground. The swing phase is period of time in which the foot is off the ground in swinging forward in walking.

As illustrated in FIG. 2 the microcomputer 24 includes a small speaker 50 or sound buzzer that alerts a clinician and/or patient each time that a target weight is exceeded. The loudness of the buzzer is controlled by a regulator 52. In addition, a computer interface 54 is provided to download the data from the device to a personal computer for further analyses by a clinician or physician. A pair of buttons 56 and 58 may also be provided for storing data and clearing the microcomputer in preparation for a different patient.

FIG. 3 merely illustrates the multiple arrays of displacement transistors 61 disposed in an insole and wherein each of the transistors converts a mechanical pressure signal to an electrical signal for processing by the microcomputer 24. The area 62 is an illustration of a load as sensed by the transistors when pressure is applied by the foot.

A displacement transistor 64 of a type used in the present invention is shown in FIG. 4. As shown, the transistor is a mechanical resonator made from gallium arsenide (GaAs) and is based on detecting the piezoelectrically induced charge. Changing pressure (caused by the foot stepping onto the ground) causes changes inside of piezoelectrically capacitance and the applied voltage to change. In this way, the patient and clinician learn how much weight is applied by each foot. Also, when a target weight is exceeded the buzzer sounds.

As shown the displacement transistor 64 is a block that contains a GaAs mechanical resonator. The direction of pressure caused by the displacement of pressing a foot on the ground as in a gait cycle is indicated by the arrows 65. "BcC" indicates a power supply for electronic circuits while "corn" is a common lead between a power supply and data output. The signal out is a variation of voltage output that feed the computer and alerts a patient.

Figure 5:
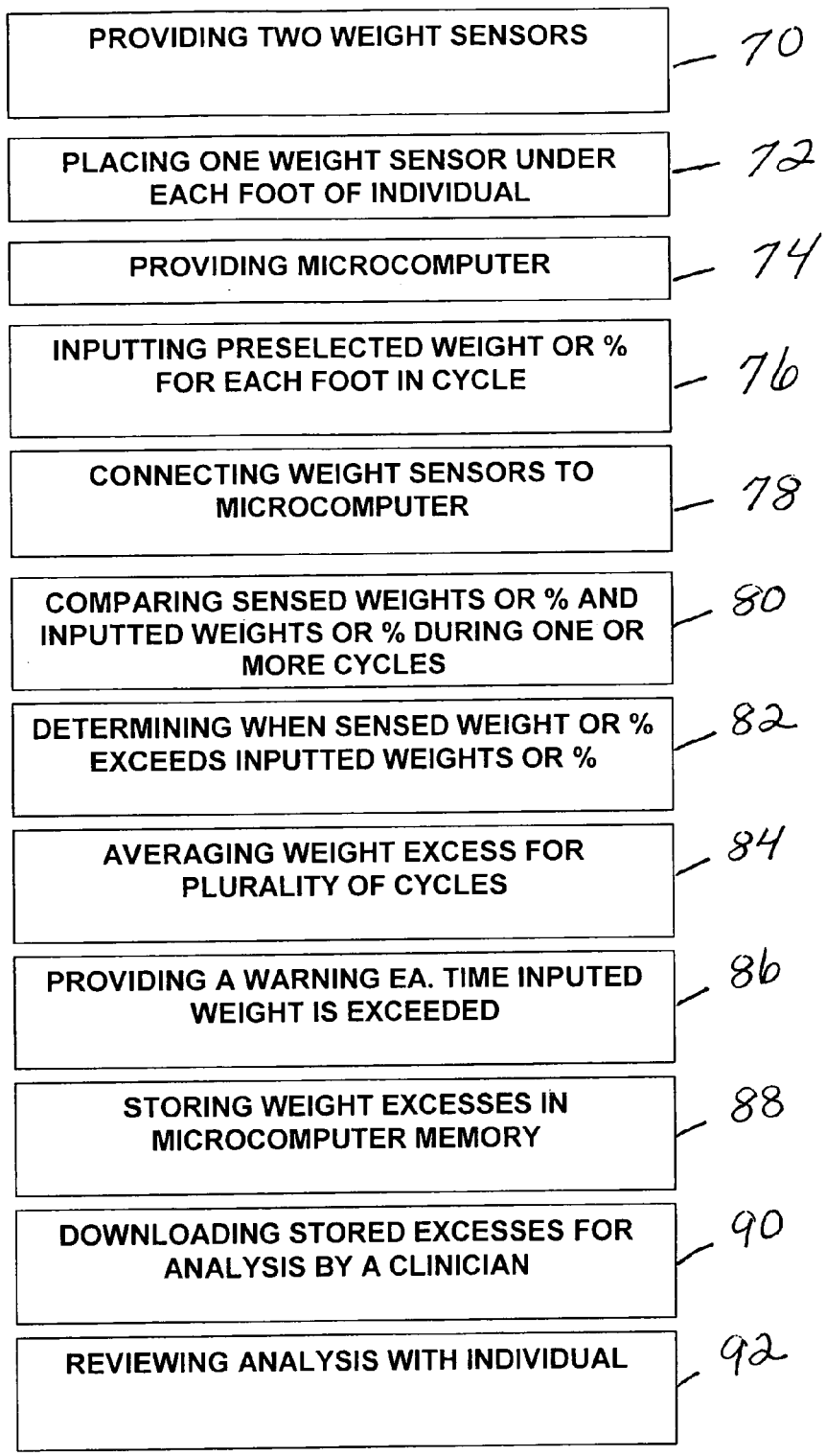
FIG. 5 is a flow chart for a method for detecting and/or correcting improper weight distribution in accordance with a further embodiment of the invention.

A gait training method for detecting and correcting improper weight distribution while walking in accordance with a preferred embodiment of the invention will now be described in connection with FIG. 5. As shown in FIG. 5, the method includes the step 70 of providing two weight sensors and placing one weight sensor under each foot of an individual or patient in step 72. The method also includes the steps 74 of providing a microcomputer, the step 76 of inputting pre-selected target weights and/or percentages for each foot into the microcomputer's memory and the step 78 of connecting the weight sensors to the microcomputer.

The sensed weights and/or weight percentages for each foot are compared to the inputted target weight or percentage during one or more gait cycles in step 80 and determining when the sensed weights or percentages for each foot exceed the target weights or percentages in step 82. In the preferred embodiment of the invention, the weights in excess of the target weight are averaged in step 84. A warning is provided or sounded each time that a target weight is exceeded in step 86 and the weight or percentage excess stored in the microcomputer's memory in step 88. In step 90, the stored weight excesses or percentages together with the actual weights applied are downloaded and printed or displayed on a monitor for analyzing by a clinician in step 92 for reviewing with the individual being tested.

A further advantage of the devices and method in accordance with the present invention resides in those cases where an individual has a spinal problem or fractures in both limbs. In such cases it is believed that the use of percentages may be helpful in counseling a patient to use aids such as canes or the like and to apply the proper amount of weight to each limb to enhance healing and to walk properly.

While the invention has been described in connection with the preferred embodiments it should be recognized that changes and modifications may be made therein without departing from the scope of the appended claims.

What is claimed is:

1. A gait training device for detecting and correcting improper weight distribution during movement of an individual's body, in which said device comprises:
    two weight sensors with one of said weight sensors positioned under each of an individual's two feet and each of said weight sensors producing an output signal indicative of the weight on the sensor and wherein each of said weight sensors comprises an array of displacement transistors for converting mechanical pressure into an electrical signal;
    a microcomputer and means for inputting pre-selected target weights into said microcomputer;
    a control panel including a pair of window displays for displaying the forces applied by each leg of the individual and each of said window displays divided into two areas for displaying the time that each leg spends in a stance phase and a swing phase averaged over a number of gait cycles and said control panel including a pair of target weight selectors wherein each of said selectors include an up and down indicator for increasing or decreasing a target weight;
    a timer including an indicator, a start button and a reset button to measure the time of a session including multiple gate cycles on said control panel and a second set of buttons on said control panel for storing data and clearing said microcomputer in preparation for a different patient;
    a pair of cables connecting said weight sensors and said control panel to said microcomputer;
    said microcomputer including means for comparing the pre-selected weight and the sensed weight and computer memory that allows a clinician to monitor weight bearing data during a selected period of time, and also a speaker or sound buzzer that alerts a clinician and/or patient each time that a target weight is exceeded;
means for indicating differences between pre-selected weights and sensed weights; and
means for transferring the data from the gait training device to a personnel computer; which includes memory means for storing the weight distribution during multiple gait cycles and means for reviewing the memory for analyses by a clinician; and
in which said weight sensors are Galium Arsenide displacement transistors.

* * * * *